United States Patent [19]

Naijoh et al.

[11] Patent Number: 5,229,032

[45] Date of Patent: Jul. 20, 1993

[54] PROCESS FOR PRODUCING AN OPTICALLY ACTIVE BENZOIC ACID DERIVATIVE

[75] Inventors: Shuichi Naijoh; Chozo Inoue; Ayako Kurotaki; Kimie Nagai, all of Tokyo, Japan

[73] Assignee: Showa Denko K.K., Tokyo, Japan

[21] Appl. No.: 828,224

[22] Filed: Jan. 30, 1992

Related U.S. Application Data

[62] Division of Ser. No. 717,579, Jun. 19, 1991, abandoned, which is a division of Ser. No. 435,872, Nov. 14, 1989, Pat. No. 5,055,225.

[30] Foreign Application Priority Data

Nov. 14, 1988 [JP] Japan .................................. 63-28849

[51] Int. Cl.$^5$ ..................... C09K 19/12; C09K 19/20; C07C 321/00
[52] U.S. Cl. .......................... 252/299.65; 252/299.64; 252/299.67; 560/18
[58] Field of Search ....................... 252/299.01, 299.64, 252/299.65, 299.67; 560/18

[56] References Cited

U.S. PATENT DOCUMENTS

| | | | |
|---|---|---|---|
| 4,828,754 | 5/1989 | Takehara et al. | 252/299.65 |
| 4,876,027 | 10/1989 | Yoshinga et al. | 252/299.65 |
| 4,943,385 | 7/1990 | Inoue et al. | 252/299.67 |
| 4,943,386 | 7/1990 | Takehara et al. | 252/299.65 |
| 5,034,152 | 7/1991 | Katagiri et al. | 252/299.65 |
| 5,055,225 | 10/1991 | Naijoh et al. | 252/299.65 |

Primary Examiner—Robert L. Stoll
Assistant Examiner—Philip Tucker
Attorney, Agent, or Firm—Sughrue, Mion, Zinn, Macpeak & Seas

[57] ABSTRACT

An optically active benzoic acid derivative represented by formula (I):

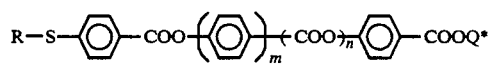

wherein R represents a straight chain alkyl group having 6 to 14 carbon atoms; Q* represents an optically active branched chain alkyl group having an asymmetric carbon atom; and m and n each represents an integer of 0 or 1, provided that m is not 0 when n is 1, a process for the production thereof, and a liquid crystal device element using the same are disclosed. The benzoic acid derivative exhibits a chiral smectic phase over a wide temperature range, a large spontaneous polarization and a high speed response.

6 Claims, No Drawings

PROCESS FOR PRODUCING AN OPTICALLY ACTIVE BENZOIC ACID DERIVATIVE

This is a divisional of Application No. 07/717,579, filed June 19, 1991, now abandoned which is a Divisional Application of Application No. 07/435,872, filed Nov. 14, 1989 now U.S. Pat. No. 5,055,225.

FIELD OF THE INVENTION

This invention relates to a novel alkyl thiobenzoate derivative having a liquid crystal property, a process for producing the compound and a liquid crystal display element using the compound. The compound of the present invention is a novel liquid crystal compound which shows a ferroelectricity (chiral smectic C phase) by itself and is thus available as a constituent of a ferroelectric liquid crystal display element to be used as an electrooptical switching element.

BACKGROUND OF THE INVENTION

There have been known a number of liquid crystal compounds including those which are called nematic liquid crystals. Although compounds or compositions mainly employed in liquid crystal display devices at present comprises these nematic liquid crystals, they have a serious disadvantage, namely, a low response speed of a several millisecond order. Thus it is considered that the enlargement of these display devices might be restricted thereby.

In order to improve this disadvantage of conventional liquid crystal display devices, N. A. Clark and S. T. Lagerwall proposed to use liquid crystals having a bistability, as described in JP-A-56-107216. (The term "JP-A" herein used means an "unexamined published Japanese patent application".) These liquid crystals having a bistability are called ferroelectric liquid crystals and attract public attention since they can give high response and memory properties. Recently, it has been frequently attempted to put these ferroelectric liquid crystals into practical use. Thus it has been urgently required to develop practically available ferroelectric liquid crystal materials.

Generally speaking, the ferroelectricity is actualized with compound having an optically active moiety in a smectic phase where the long axis of the molecule shows an orientation tilting against the normal direction of the layer made of the compound. A chiral smectic phase (hereafter referred to as $S_c^*$) is particularly advantageous from a practical viewpoint since the driving voltage thereof is relatively low.

Thus ferroelectric liquid crystals exhibit an extremely high response due to spontaneous polarization, can express a bistable state of high memory properties, has an excellent viewing angle, and are suitable for a display material of a large capacity and a large picture.

A known example of such ferroelectric liquid crystal compounds is (S)-2-methylbutyl 4-(4-decyloxybenzylideneamino)cinnomate (hereafter referred to as DOBAMBC) synthesized by R. B. Meyer et al. as described in J. Physicue, 36 L-69 (1975).

This DOBAMBC contains a Schiff base in its structure, which causes a problem in chemical stability. Therefore there has been attempted to find out ferroelectric liquid crystal compounds which are physically and chemically stable Now the main current of these studies goes toward esters such as (S)-2-metybutyl 4-(4-n-alkoxybenzoyloxy)benzoate (hereafter referred to as CN). However, these esters would show either no $S_c^*$ phase or an $S_c^*$ phase, if any, within a considerably narrow temperature range. Furthermore, they are monotropic liquid crystals whose phase system achieved by heating the liquid crystals to a certain temperature differs from that achieved by cooling the same to the same temperature. Accordingly there are only a few compounds which are practically applicable, as described in *Liquid Crystals and Ordered Fluids*, 4 (1984).

On the other hand, there have been known sulfur-containing liquid crystal compounds such as ferroelectric liquid crystals having thioester groups, for example, alkyl thioesters as described in *Liquid Crystals and Ordered Fluids*, 4 (1984) and phenyl thioesters as described in JP-A-62-205056, JP-A-62-281854 and JP-A-63-27451, and ferroelectric liquid crystals containing alkyl thiophenylpyrimidine structures as described in JP-A-62-292766.

However, each of these compounds either shows a narrow $S_c^*$ phase temperature range or forms monotropic liquid crystals. Thus it has not been effective to introduce a sulfur atom to the skeleton in the preparation of ferroelectric liquid crystal compounds.

Accordingly, it has been required to develop ferroelectric liquid crystals which have a wide $S_c^*$ phase temperature range, compared with ester-type ferroelectric liquid crystals or known sulfur-containing ones, and are not monotropic.

SUMMARY OF THE INVENTION

An object of the present invention is to provide a liquid crystal compound which is applicable for ferroelectric liquid crystal display element and satisfies the following requirements (i) showing an extremely high chemical stability, (ii) showing an $S_c^*$ phase over a wide temperature range, (iii) having a low viscosity caused by its structure, (iv) showing a large spontaneous polarization originating from a carbonyl group, and (v) showing a high-speed response against an applied electric field.

Another object of the present invention is to provide a process for producing the liquid crystal compound.

Still another object of the present invention is to provide a liquid crystal display element using the liquid crystal compound.

In order to satisfy these requirements, the present inventors turned attention to the physical properties of sulfur atom, for example, the low electronegativity comparable to that of carbon atom and the bending angle of the sulfide bond of 96°, which has never been considered, and as a result of extensive study it has been found that compounds showing a wide $S_c^*$ phase temperature range from a low temperature can be obtained by utilizing the abovementioned properties of sulfur atom.

That is, the present invention is a novel alkyl thiobenzoate derivative represented by formula (I)

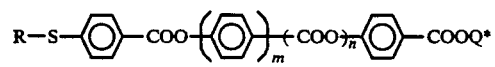

wherein R represents a straight chain alkyl group having 6 to 14 carbon atoms, Q* represents an optically active branched chain alkyl group having an asymmetric carbon atoms, and m and n each represents an integer of 0 or 1, provided that m is not 0 when n is 1.

DETAILED DESCRIPTION OF THE INVENTION

In formula (I), the alkyl group for R preferably has 6 to 10 carbon atoms, and the optically active alkyl group for Q* preferably has 4 to 8 carbon atoms.

In the present invention, the properties of sulfur atom can contribute to actualization of the $S_c^*$ phase and the ferroelectricity due to the thioether group wherein the alkyl group of R is bound to a benzoate group via a sulfur atom.

That is to say, the present invention has been achieved by utilizing the low electronegativity of sulfur atom, which is comparable to that of carbon atom, to increase the dipole moment of the carbonyl group in the neighborhood of the asymmetric carbon atom and also utilizing the bending angle of the sulfide (96°) to make it easy to tilt liquid crystal molecules in the phase and form a helical structure.

The compounds of the present invention having an alkylthiobenzoate group and an optically active alkyl group containing a asymmetric carbon atom bound to a phenyl group are novel and may be prepared by reacting an alkylthiobenzoic acid represented by formula (II)

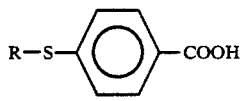
(II)

(wherein R represents a straight chain alkyl group having 6 to 14 carbon atoms) or a reactive derivative thereof with a compound represented by formula (III)

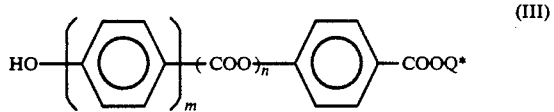
(III)

(wherein Q* represents an optically active branched chain alkyl group having an asymmetric carbon atom, and m and n each represents an integer of 0 or 1, provided that m is not 0 when n is 1).

The alkylthiobenzoic acid represented by formula, (II) can be synthesized only with difficulty and is not easily available. However, it has now been found that it can be produced by reacting p-aminobenzoic acid which is inexpensive, with sodium nitrite in an aqueous solution of hydrochloric acid to form a diazonium salt and then directly reacting the diazonium salt with mercaptane without isolating the diazonium salt.

More specifically, p-aminobenzoic acid is dissolved in 2 equivalents or more of hydrochloric acid to form an amine salt of hydrochloric acid in an acidic condition, followed by gradually adding one equivalent of sodium nitrite to the reaction mixture while cooling with ice water to a temperature of 0 to 5° C. After the reaction mixture becomes clear and yellow to form a diazonium salt, the reaction mixture is neutralized with sodium acetate with further cooling. Then, an equivalent of alkylmercaptane is added to the diazonium salt solution under an alkaline condition with a sodium hydroxide aqueous solution and the like, wherein the reaction proceeds with generation of nitrogen gas. It is desired that the reaction be carried out at a temperature (room temperature) at which nitrogen gas is not abruptly generated. After the reaction is completed, the reaction product (sodium salt) is dissolved in a solvent, followed by adding a mineral acid in the resulting solution to precipitate an alkylthiobenzoic acid.

This is a novel process for production of the alkylthiobenzoic acid without using any mercaptobenzoic acid compounds as an intermediate, whereby thioether groups of various alkyl chain lengths can be readily obtained. Namely, this process first makes it possible to introduce an alkylthiobenzoate group into a liquid crystal structure, and makes it easy to control the kind and temperature range of liquid crystal phases by way of changing the length of the alkyl chain of the liquid crystal compound.

Examples of the substituent R in the compound of formula (II) include hexyl, heptyl, octyl, nonyl, decyl, undecyl, dodecyl, tridecyl and tetradecyl groups.

The compound of formula (III) may be prepared by using 4-hydroxybenzoic acid or 4'-(4-hydroxyphenyl)-benzoic acid as a starting material, and performing esterification of the starting material with a chiral alcohol according to the following process (1) or (2), or process (3) wherein the hydroxy group of the starting material is protected with a benzyl group before the esterification and debenzylation is performed after the esterification.

(1) The esterification is performed in the presence of an equivalent or less of acid catalyst such as sulfuric acid and p-toluenesulfonic acid under reflux for several hours.

(2) The esterification is performed at not higher than room temperature using, as a condensing agent, an equivalent of N,N'-dicyclohexylcarbodiimide (hereafter referred to as DCC) or water-soluble DCC.

(3) Alkyl 4-hydroxybenzoates or alkyl 4'-(4-hydroxyphenyl)benzoates are reacted with an equivalent of benzyl bromide using a solvent in an alkaline condition with the addition of an equivalent or more of potassium hydroxide, sodium hydroxide or the like under reflux for several hours. Then, the resulting solution is added in an excess alkaline aqueous solution and the mixture is stirred at room temperature to hydrolyze the esters, whereby 4-benzyloxybenzoic acid or 4'-(4-benzyloxyphenyl)benzoic acid is obtained. Thereafter, the thus benzyl-protected compound is subjected to condensation reaction with a chiral alcohol according to the above process (1) or (2), or the following manner that the benzyl-protected compound is reacted with not less than an equivalent of thionyl chloride, phosphorus pentachloride or oxalyl chloride under reflux to obtain a corresponding acid chloride which is then reacted with an equivalent of a chiral alcohol in the presence of not less than an equivalent of bases such as pyridine and triethylamine for several hours at room temperature; and then the produced chiral alkyl ester of the 4-benzyloxybenzoic acid or 4'-(4-benzyloxyphenyl)benzoic acid is subjected to debenzylation by a catalytic reduction process e.g., using a palladium-carbon catalyst carrying 1 to 10 wt% of activated palladium black on carbon powder in the stream of hydrogen or organic hydrogen donors such as cyclohexene and 1,4-cyclohexadiene.

The reaction between the compound of formula (II) and that of formula (III) may be conducted using a solvent such as ethyl acetate, toluene, benzene, xylene, ether, hexane, tetrahydrofuran, methylene chloride and carbon tetrachloride in the same manner as in the above process (1) or (2). Alternately, a reactive derivative of the compound of formula (II) may be reacted with the compound of formula (III) in the presence of an equivalent or more of bases such as pyridine and triethylamine at room temperature for several hours. Examples of the reactive derivative include acid halides such as acid chlorides which may be obtained by reacting the alkylthiobenzoic acid of formula (II) with an equivalent or more of thionyl chloride, phosphorus pentachloride or oxalyl chloride under reflux.

Even though sulfur atom is introduced into the structure of ferroelectric liquid crystal compounds, the compound thus prepared unexpectedly show no increase in melting point. Thus it shows scarcely any change as compared with the case wherein oxygen atom is introduced. Further, the compound shows a ferroelectricity over a wide temperature range.

The compound of formula (I) according to the present invention is a liquid crystal compound which is an alkylthiobenzoate derivative having a sulfur atom in the form of thioether group.

When the thioether group is a long-chain in particular, the bond angle of a flexible group with a core group containing the benzoate can be decreased by approximately 10°, compared with that of an ether bond, making the compound possible to readily tilt in the molecular layer and to show a ferroelectricity over a wide temperature range.

Thus the compound of the present invention is a ferroelectric liquid material which is applicable to a liquid crystal display element excellent in response and memory properties.

Furthermore, the compound of the present invention can be blended with a known liquid crystal compound to thereby actualize the ferroelectricity and to expand the ferroelectricity temperature range or improve the response properties.

The compound of the present invention will be described in detail with reference to the following Examples but the present invention is not limited thereto.

In the Examples, Crys, $S_B$, $S_X^*$, $S_C^*$, $S_A$, Iso and Ch phases respectively represent a crystal phase, a smectic B phase, a chiralsmectic phase (not identified), a chiral smectic C phase, a smectic A phase, an isotropic phase and a cholesteric phase.

The compound of the present invention was purified by silica gel chromatography and recrystallized from an alcohol and hexane. The determination of the phase transition temperatures may be somewhat affected by purity of the compound.

EXAMPLE 1

Synthesis of (S)-2-methylbutoxycarbonyl 4-n-decylthiobenzoyloxybiphenyl-4'-carboxylate (1-a)

Synthesis of 4-n-decylthiobenzoic acid 10.3 g of p-aminobenzoic acid, 15.0 g of conc hydrochloric acid and 30.0 ml of water were heated to 50° C. under vigorously stirring. The temperature of the suspension thus obtained was cooled to about 0° C. 5.18 g of sodium nitrite dissolved in the minimum amount of water was added to the above suspension to thereby give a diazo compound. During this process, ice was added, if required, so as to maintain the suspension temperature from 0° to 5° C. When the reaction mixture became yellow and transparent, the reaction was completed. Then the pH of the reaction mixture was adjusted to 6 with a cold saturated aqueous solution of sodium acetate. The formed precipitate, if any, was filtered. 13.1 g of decylmercaptane was dissolved in a solution of 6.00 g of sodium hydroxide in 30.0 ml of water, to which the abovementioned diazonium salt solution was slowly dropwise added with stirring at a temperature of 0° to 5° C. After completion of the addition, the reaction mixture was heated to 60° C. over 1 hour and then continued the stirring at 60° C. for 2 hours. Thus a vigorous reaction took place with generation of nitrogen gas. After completion of the generation of nitrogen, the mixture was cooled and the brown solid matter was filtered. 500 ml of water and 50 ml of 2-propanol were added to the solid matter which was then dissolved therein by heating to 70° C. under stirring. Next, 10 wt% sulfuric acid was added to thereby adjust the pH of the mixture to 1 or below. After cooling to 5° C., a precipitate was obtained. The precipitate was then recrystallized from 300 ml of n-hexane and 200 ml of methanol. Thus 8.20 g of 4-decylthiobenzoic acid was obtained as colorless needle-like crystal (yield: 37%).

IR: 2930, 1680, 1600, 1420 and 1290 cm$^{-1}$ $^1$H-NMR: 0.90, 1.28, 3.00, 7.30 and 7.98 ppm (1-b)

Synthesis of (S)-2-methylbutyl 4-hydroxybiphenyl-4'-carboxylate:

3.75 g of 4-hydroxybiphenyl-4'-carboxylic acid was heated under reflux together with (S)-2-methylbutyl alcohol in the presence of 0.10 g of p-toluenesulfonic acid for about 6 hours. Then the mixture was filtered to remove the unreacted 4-hydroxybiphenyl-4'-carboxylic acid. Next, the filtrate was evaporated and the unreacted (S)-2-methylbutyl alcohol was distilled off. The crystals thus obtained were recrystallized from 200 ml of n-hexane. Thus, 2.05 g of the corresponding colorless compound was obtained (Yield: 41%).

(1-c)

Synthesis of (S)-2-methylbutoxycarbonyl 4-n-decylthiobenzoyloxybiphenyl-4'-carboxylate:

4.00 g of the n-decylthiobenzoic acid prepared in (1-a) was heated under reflux together with 16.2 g of thionyl chloride in 50 ml of carbon tetrachloride for 3 hours. Then the unreacted thionyl chloride and carbon tetrachloride were distilled off to obtain a yellow oily substance. To the reaction solution was added a solution which was prepared by dissolving 3.90 g of the (S)-2 methylbutyl 4-hydroxybiphenyl-4'-carboxylate obtained in (1-b) in 100 ml of toluene. Further, 5.40 g of pyridine was added thereto and the resulting mixture was stirred at 80° C. for 3 hours. After completion of the reaction, 100 ml of ethyl acetate and 200 ml of 5 wt% hydrochloric acid were added to extract the reaction product with the ethyl acetate. Furthermore, a 5 wt% aqueous solution of sodium hydrogencarbonate was added to the ethyl acetate phase and the mixture was extracted with ethyl acetate. The ethyl acetate phase was washed with 100 ml of a saturated aqueous solution of common salt and then dried over anhydrous sodium sulfate. The ethyl acetate was distilled off and the residue was subjected to silica gel column chromatography using a mixture of n-hexane and ethyl acetate (mixing ratio: 5/1 by volume) as an eluent to obtain colorless crystals. Further, these crystals were recrystallized from n-hexane and methanol. Thus 3.10 g of (S)-2-methylbutoxycarbonyl 4-n-decylthiobenzoyloxybiphenyl-4'-carboxylate was obtained. The structure of this product was confirmed based on the following data.

¹H-NMR 0.85, 3.40, 4.21, 7.27 and 8.15 (ppm)
Mass spectrum: m/z: 560 (M+)

| Elemental analysis: | C | H | S |
|---|---|---|---|
| Calculated (%) | 74.96 | 7.91 | 5.72 |
| Found (%) | 74.22 | 7.78 | 5.50 |

The thus synthesized (S)-2-methylbutoxycarbonyl 4-n decylthiobenzoyloxybiphenyl-4'-carboxylate was sandwiched between two glass plates provided with transparent electrodes to form a cell having a thickness of 3.3 μm. More specifically, the compound was heated to give an isotropic liquid. The obtained liquid was injected into two transparent glass electrodes with a spacer of 3.3 μm in thickness by vacuum-injection to thereby prepare a film cell. Then the cell was cooled at a rate of 0.5° C. per minute and the SA phase was aligned by the spacer edge method as described in K. Kondo et al, *Jpn. J. Appl. Phys.*, 22 L85 to 87 (1983). It was further cooled to 109.3° C. or below and thus a homogeneous domain where the helical structure disappeared was obtained.

Spontaneous polarization was measured according to the triangular voltage wave method as described in Fukuda et al. *Ferroelectrics*, 58, 55 (1984), and it was 4.0 nC/cm² at 99° C. which was 10° C. below the upper limit temperature (109.3° C.) of the So* phase. Further when rectangular wave (±5 V, 1000 Hz) was applied to the cell at 90° C., a rapid and clear response of about 200 μsecond was obtained.

EXAMPLE 2

Synthesis of (S)-2-methylbutoxycarbonyl 4-n-dodecylthiobenzoyloxybiphenyl-4-'carboxylate (2-a)

Synthesis of n-dodecylthiobenzoic acid

The procedure of (1-a) was repeated except that dodecylmercaptan was used in place of decylmercaptan. The NMR and IR data of the n-dodecylthiobenzoic acid thus obtained were almost the same as those of the product obtained in (1-a), though the intensity ratio of the peak corresponding to a methylene chain differed.

(2-b)

Synthesis of (S)-2-methylbutoxycarbonyl 4-n-dodecylthiobenzoyloxybiphenyl-4'-carboxylate:

The procedure of (1-c) was repeated except that n-dodecylthiobenzoic acid was used in place of n-decylthiobenzoic acid. The NMR data of the product thus obtained were almost the same as those of the product obtained in (1-c), though the intensity ratio of the peak corresponding to a methylene chain differed.

EXAMPLE 3

Synthesis of 4-((S)-2-methylbutoxycarbonyl)phenyl 4-(4dodecylthiobenzoyloxy)benzoate (3-a)

Synthesis of 4-((S)-2-methylbutoxycarbonyl)phenyl 4-hydroxybenzoate 6.54 9 of p-benzyloxybenzoic acid was heated under reflux together with 12.5 g of thionyl chloride in 40 ml of carbon. tetrachloride for 3 hours. Then the unreacted thionyl chloride and carbon tetrachloride were distilled off to obtain a yellow oily residue. A solution obtained by dissolving 1.64 g of (S)-2-methylbutyl alcohol in 40.0 ml of toluene was added to the oily residue and the resulting mixture was heated under reflux for 3 hours. After completion of the reaction, 30.μ ml of ethyl acetate and 100 ml of 5 wt% hydrochloric acid were added to the reaction mixture to extract the reaction product with the ethyl acetate. Further, the ethyl acetate phase was washed with 100 ml of a 5 wt% aqueous solution of sodium hydrogencarbonate and a saturated aqueous solution of common salt and then dried over anhydrous sodium sulfate. The ethyl acetate was distilled off and the residue was subjected to silica gel column chromatography with a mixture of n-hexane and ethyl acetate (mixing ratio: 10/1 by volume) as an eluent. Thus 4.49 g of a colorless oily substance was obtained. Then the oily substance was dissolved in 15 ml of ethanol and heated under reflux in the presence of 6.75 g of cyclohexene and 0.45 g of palladium black for 1 hour. Then the palladium black was removed by filtering the reaction mixture and the ethanol and cyclohexene were distilled off. The colorless oily substance thus obtained was dissolved in 80.0 ml of toluene, washed with 20.0 ml of water and dried over anhydrous sodium sulfate. The toluene was distilled off to thereby obtain 2.99 g of (S)-2-methylbutyl 4-hydroxybenzoate (yield: 93%).

Next, 0.80 g of p-benzyloxybenzoic acid was heated under reflux together with 4.17 g of thionyl chloride in 15 ml of carbon tetrachloride for 3 hours. Then the unreacted thionyl chloride and carbon tetrachloride were distilled off to obtain a yellow oily substance. A solution prepared by dissolving 0.73 g of the above-prepared (S)-2-methylbutyl 4-hydroxybenzoate in 7.00 ml of toluene was added to the oily substance. Further, 3.50 g of pyridine was added and the resulting mixture was stirred at 80° C. for 3 hours. After completion of the reaction, 30.0 ml of ethyl acetate and 50.0 ml of 5 wt% hydrochloric acid were added to extract the reaction product with the ethyl acetate. The ethyl acetate phase was washed with 50.0 ml of a 5 wt% aqueous solution of sodium hydrogencarbonate and a saturated aqueous solution of common salt and dried over anhydrous sodium sulfate. The ethyl acetate was distilled off and the residue was recrystallized from methanol to obtain 0.89 g of 4-((S)-2-methylbutoxycarbonyl)phenyl 4-benzyloxybenzoate. Then this product was dissolved in 10.0 ml of ethanol and heated under reflux in the presence of 1.01 g of cyclohexene and 0.18 g of palladium black for 1 hour. The palladium black was removed by filtering the reaction mixture and the ethanol and cyclohexene were distilled off. Thus 0.69 g of 4-((S)-2-methylbutoxycarbonyl)phenyl 4-hydroxybenzoate was obtained.

(3-b)

2.00 g of the n-dodecylthiobenzoic acid obtained in (2-a) was heated under reflux together with 14.9 g of thionyl chloride in 50 ml of carbon tetrachloride for 3 hours. Then the unreacted thionyl chloride and carbon tetrachloride were distilled off to obtain a yellow oily substance. Next, 2.04 g of the 4-((S)-2-methylbutoxycarbonyl)phenyl 4-hydroxybenzoate obtained in (3-a) dissolved in 50.0 ml of toluene was added to the oily substance. Further, 4.90 g of pyridine was added and the resulting mixture wag stirred at 80° C. for 3 hours. After completion of the reaction, 100 ml of ethyl acetate and 200 ml of 5 wt% hydrochloric acid were added to extract the reaction product with the ethyl acetate. The ethyl acetate phase was washed with 1μml of a 5 wt% aqueous solution of sodium hydrogencarbonate and a saturated aqueous solution of common salt and dried over anhydrous sodium sulfate. The ethyl acetate was distilled off and the residue was recrystallized from n-hexane. Thus 2:00 g of 4 ((S)-2-methylbutoxycarbonyl)phenyl 4-(4-dodecylthiobenzoyloxy)benzoate was obtained (yield: 50%).

EXAMPLES 4 TO 12

Compounds represented by formula (I), which were different in alkyl chain length for R, number of benzene ring, number of ester bond, optically active groups for Q*, for example, (S)-2-methylbutyl, (S)-1-methylheptyl and (S)-1-methylbutyl groups, as shown in Table 1, were synthesized in a similar manner to those mentioned in Examples 1 to 3. The thus obtained compounds showed $S_c^*$ over a wide temperature range, which had been never observed in conventional sulfur-containing ferroelectric liquid crystals.

Further, cells was prepared in the same manner as in Example 1 except using the compound of Example 4 ((S)-2-methylbutoxycarbonyl 4-n-octylthiobenzoyloxybiphenyl-4'-carboxylate) and the compound of Example 8 ((S)-2-methylbutoxycarbonyl 4-n-hexylthiobenzolyloxybiphenyl-4-'-carboxylate), respectively, and their spontaneous polarizations were measured as in Example 1. As a result, they were 2.7 nC/cm² at 97.5° C. and 1.8 nC/cm² at 91.5° C., respectively.

When the latter cell, i.e., using the compound of Example 8 was placed between two polarizers which fell at right angles with each other and an alternating electric field of ±15 volts was applied to the cell, change in intensity of transmitted light was observed, from which the response speed of the cell was found to be about 60 μ second at 90° C.

The upper limit temperatures of the respective phases of the compounds prepared in Examples 1 to 12 are shown in Table 1 below.

A: (disclosed in JP-A-63-122651)

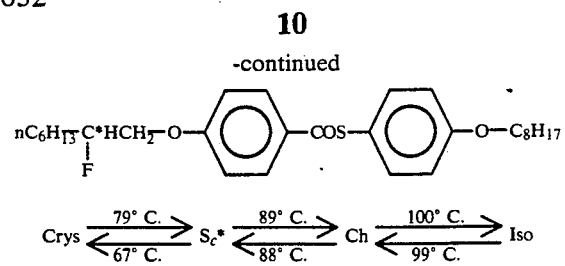

B: (disclosed in JP-A-62-292766)

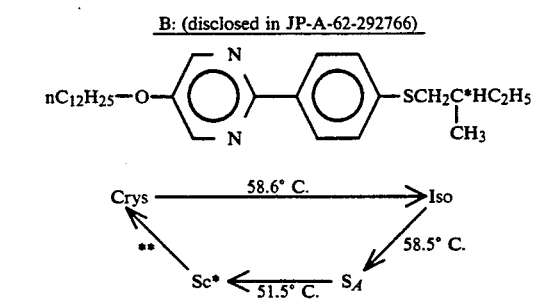

C: (disclosed in JP-A-63-27451)

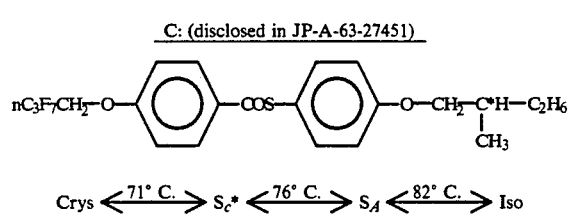

As described above, the compound of the present invention shows a ferroelectricity over an extremely wide temperature range. Thus it can be used either alone or in the form of composition with other appropriate nematic, smectic or ferroelectric liquid crystals to economically provide useful materials for liquid crystal display element.

While the invention has been described in detail and with reference to specific embodiments thereof, it will be apparent to one skilled in the art that various changes and modifications can be made therein without departing from the spirit and scope thereof.

What is claimed is:

1. A process for producing an optically active benzoic acid derivative represented by formula (I):

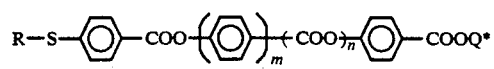

TABLE 1

| Example NO. | R | m | n | Q | Upper Limit Temperature *1 (°C.) | | | | | |
|---|---|---|---|---|---|---|---|---|---|---|
| | | | | | Crys | $S_B$ | $S_X^*$ | $S_c^*$ | $S_A$ | Ch |
| 1 | n-C$_{10}$H$_{21}$ | 1 | 0 | —CH$_2$—C*H(CH$_3$)C$_2$H$_5$ | 73.5 | | | 109.3 | 148 | |
| 2 | n-C$_{12}$H$_{25}$ | 1 | 0 | —CH$_2$—C*H(CH$_3$)C$_2$H$_5$ | 69.7 | | | 104.8 | 143.7 | |
| 3 | n-C$_{12}$H$_{25}$ | 1 | 1 | —CH$_2$—C*H(CH$_3$)C$_2$H$_5$ | 77.0 | | | | 128.0 | |
| 4 | n-C$_8$H$_{17}$ | 1 | 0 | —CH$_2$—C*H(CH$_3$)C$_2$H$_5$ | 61.5 | | | 107.5 | 146.7 | |
| 5 | n-C$_{12}$H$_{25}$ | 0 | 0 | —CH$_2$—C*H(CH$_3$)C$_2$H$_5$ | 37.9 | | | | (53.0) | |
| 6 | n-C$_{12}$H$_{25}$ | 1 | 0 | —C*H(CH$_3$)C$_6$H$_{13}$ | 85.6 | 95.7 | 107.3 | | 123.3 | |
| 7 | n-C$_{12}$H$_{25}$ | 1 | 1 | —C*H(CH$_3$)C$_3$H$_7$ | 82.6 | (106.0)*2 | | | 125.7 | |
| 8 | n-C$_6$H$_{13}$ | 1 | 0 | —CH$_2$—C*H(CH$_3$)C$_2$H$_5$ | 60.2 | | 87.4 | 101.5 | 147.5 | 148.2 |
| 9 | n-C$_{10}$H$_{21}$ | 1 | 0 | —C*H(CH$_3$)C$_6$H$_{13}$ | 75.7 | | 75.9 | | 98.7 | |
| 10 | n-C$_{12}$H$_{25}$ | 1 | 0 | —C*H(CH$_3$)C$_3$H$_7$ | 75.0 | | 98.0 | | 107.0 | |
| 11 | n-C$_6$H$_{13}$ | 1 | 0 | —C*H(CH$_3$)C$_3$H$_7$ | 80.1 | | 80.3 | | 122.8 | |
| 12 | n-C$_6$H$_{13}$ | 1 | 0 | —C*H(CH$_3$)C$_6$H$_{13}$ | 62.8 | | | | 113.9 | |

Note
*1 Phase transition temperature when the liquid crystal compound was cooled from its Iso phase at a rate of 5° C./min.
*2 ( ) shows a monotropic phase.

COMPARATIVE EXAMPLE 1

Phase transition temperatures of typical examples A, B and C of conventional ferroelectric liquid crystals containing a sulfur atom in the structure were measured, and the results are shown below.

wherein
- R represent a straight chain alkyl group having 6 to 14 carbon atoms;
- Q* represents an optically active branched chain alkyl group having an asymmetric carbon atoms; and
- m and n each represents an integer of 0 or 1, provided that m is not 0 when n is 1, which comprises the steps of:
(i) reacting p-aninobenzoic acid with sodium nitrite to form a diazonium salt,
(ii) reacting said diazonium salt with an alkylmercaptane,
(iii) adding a mineral acid in the reaction system to precipitate an alkylthiobenzoic acid represented by formula (II):

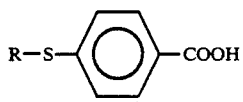

(II)

wherein R has the same meaning as above, which may be converted to a reactive derivative thereof, wherein the reactive derivative is an acid halide, and (iv) reacting said alkylthiobenzoic acid or said reactive derivative thereof with a compound represented by formula (III):

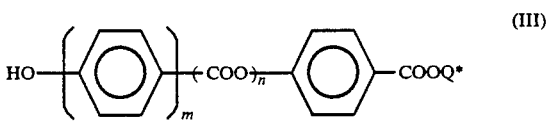

(III)

wherein Q, m and n have the same meaning as defined above.

2. The process as in claim 1, wherein the alkyl group of H has 6 to 10 carbon atoms.

3. The process as in claim 1, wherein the alkyl group of Q has 4 to 8 carbon atoms.

4. The process as in claim 1, wherein said step (i) is conducted in an aqueous solution of hydrochloric acid.

5. The process as in claim 4, wherein said step (i) is conducted by dissolving p-aminobenzoic acid in 2 equivalents or more of hydrochloric acid to form an amine salt of hydrochloric acid under an acidic condition and then adding one equivalent of sodium nitrite to the reaction system while cooling with ice water to a temperature of 0° to 5° C.

6. The process as in claim 1, wherein said step (ii) is conducted under an alkaline condition.

* * * * *